United States Patent [19]
Li et al.

[11] Patent Number: 5,419,201
[45] Date of Patent: May 30, 1995

[54] METHODS AND DEVICES FOR ELECTROCHEMICALLY DETERMINING METAL FATIGUE STATUS

[76] Inventors: Yuanfeng Li, 4107 Woodland Ave., Apt. 2F, Drexel Hill, Pa. 19026; Campbell Laird, 951 Weadley Rd., Radnor, Pa. 19087

[21] Appl. No.: 22,560

[22] Filed: Feb. 25, 1993

[51] Int. Cl.⁶ .............................................. G01N 3/32
[52] U.S. Cl. ........................................ 73/808; 73/799; 324/71.1
[58] Field of Search ................. 73/806, 808, 810, 813, 73/799; 324/693, 701, 71.1

[56] References Cited
PUBLICATIONS

Ortner et al., "The Mechanical Response of Copper Single Crystals to Corrosion–Fatigue in an Aqueous Oxide-Forming Environment", *Acta Metall.*, vol. 35, No. 2, pp. 453–462 (1987).
Ortner, Summary and Conclusions of Thesis, University of Pennsylvania, pp. 160–168 (1985).
Yan et al., "Strain Localization in Single Crystals of Copper Cycled in 0.1 M Perchloric Acid Solution Under Potential Control", *Acta Metall.*, vol. 33, No. 8, pp. 1533–1545 (1985).
Yan, Abstract of Thesis, University of Pennsylvania, pp. ii–iv (1984).
Magnin et al., "Corrosion Fatigue Mechanisms in B.C.C. Stainless Steels", *Acta Metall.*, vol. 35, No. 8, pp. 2105–2113 (1987).
Yan et al., "The Interaction of Simultaneous Cyclic Straining and Aqueous Corrosive Attack in the Behavior of Persistent Slip Bands", *Acta Metall.*, vol. 33, No. 9, pp. 1593–1600 (1985).
Pyle et al., "The Influence of Cyclic Plastic Strain on the Transient Dissolution Behavior of 18/8 Stainless Steel in 3.7M $H_2SO_4$", *Elec. Chem. Soc.*, vol. 122, No. 11, pp. 1445–1453 (1975).
Ortner et al., "The Electrochemical Response of Copper Single Crystals to Corrosion–Fatigue in an Aqueous, Oxide-Forming Environment", *Acta Metall.*, vol. 35, No. 4, pp. 867–874 (1987).
Li et al., Abstract of Thesis, "Cyclic Response–Electrochemical Interaction in Mono- and Polycrystalline AISI316L Stainless Steel", University of Pennsylvania, pp. iv–v (Mar. 2, 1992).
Li et al., proposed article, "Cyclic Response–Electrochemical Interaction in Mono- and Polycrystalline AISI 316L Stainless Steel in $H_2SO_4$ Solution: Part I", University of Pennsylvania, (unpublished).

*Primary Examiner*—Robert Raevis
*Attorney, Agent, or Firm*—Duane, Morris & Heckscher; Peter J. Cronk

[57] ABSTRACT

Devices and methods for determining the fatigue status of a metallic specimen are provided. The methods include contacting the specimen with a cell containing an electrode and an electrolyte in contact with the specimen. A voltage is then applied, or galvanically created, between the specimen and the electrode, and the current is measured passing through the electrolyte during a period in which the specimen is subjected to cyclic stresses. A signature is then prepared which is representative of a measured current at the electrode, and the signature is analyzed to determine the fatigue status of the specimen.

18 Claims, 8 Drawing Sheets

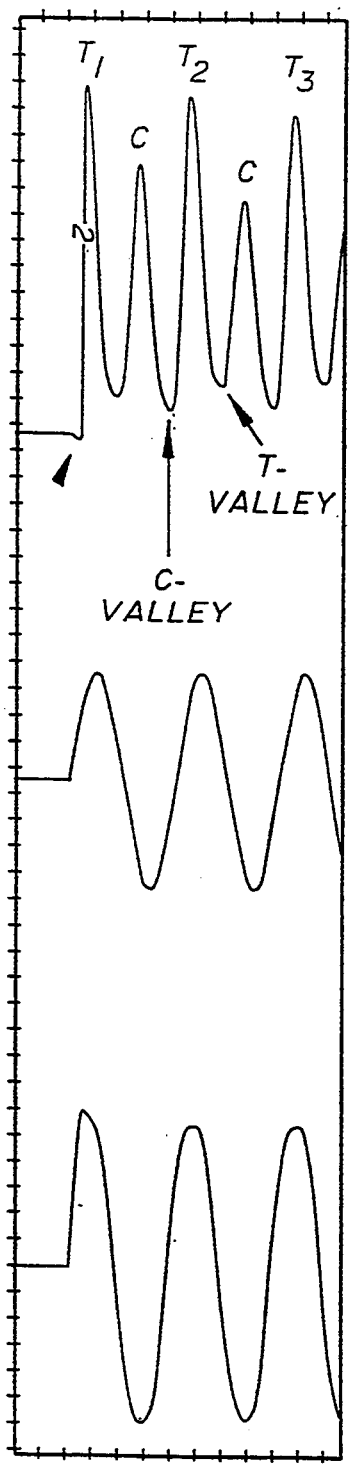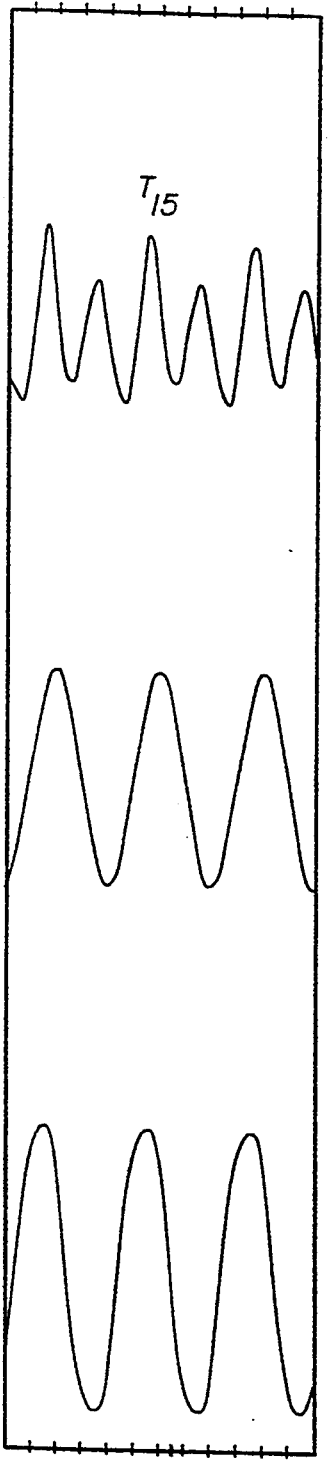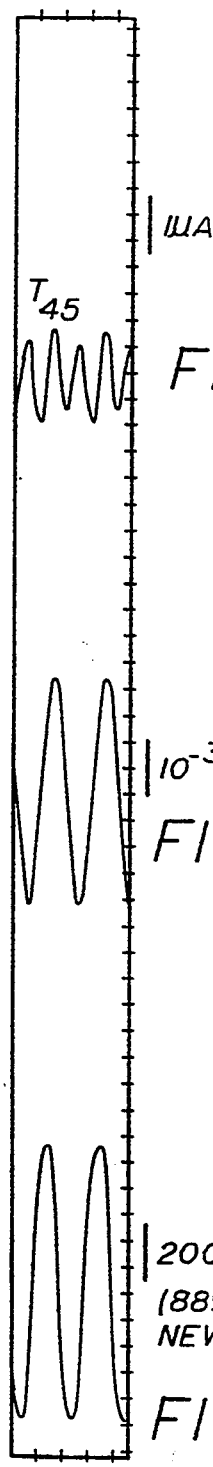
FIG 6a
FIG. 6b
FIG. 6c

METHODS AND DEVICES FOR ELECTROCHEMICALLY DETERMINING METAL FATIGUE STATUS

FIELD OF THE INVENTION

This invention relates to methods and devices for determining the degree to which metallic materials suffer fatigue damage, and more particularly, to procedures for evaluating the electrochemical interactions in metallic substrates exposed to plastic and elastic deformation.

BACKGROUND OF THE INVENTION

Many of today's modern metallic structures, such as steel bridges and aluminum airplanes, are exposed to cyclical compressive and tensile forces over their useful life. These structures have a plastic component, in which the metal undergoes deformation above its yield point, and an elastic component, in which the metal is stressed at a level below its yield point. The degree to which the metal performs over the years that it is in service is largely affected by the nature of these forces, and the corrosive environment that surrounds the metal. These environments can contain atmospheric conditions, such as acid rain and salt water, as well as man-made corrodants, such as gasoline and acids. The combination of a corrosive environment and cyclic forces creates a damage mechanism commonly referred to as "corrosion fatigue".

There are a number of techniques for measuring fatigue damage of a metal structure. Non-destructive testing, such as dye penetrant inspection, ultrasonic testing, and magnetic particle detection are just some of the more traditional techniques that have been used to determine the presence of cracks in components which have undergone fatigue damage. Although these methods are useful in forewarning catastrophic failure, they rely upon the existence of crack-like defects which are large enough to detect, and cannot perceive any other type of damage caused by cyclic stresses.

Fatigue strain gauges and fuses have also been used to predict fatigue life. Fatigue gauges rely upon monotonic changes in resistance for determining the degree of fatigue. Fatigue fuses are essentially miniature fatigue specimens attached to a structure, which undergo the same cyclical stresses as the structure and provide advanced warning of the development of fatigue damage. Although these devices have practical utility, they require advanced knowledge of an existing fatigue problem and merely provide a cumulative assessment of the damage from the onset of service life. They have little or no value in detecting the current state of damage if they were not previously affixed to the structure prior to service.

Accordingly, there is a need for a procedure for measuring fatigue damage which can be used at any point during the service life of the metallic structure, from the day it is placed in service, through the point at which it is no longer useful for its intended purpose.

SUMMARY OF THE INVENTION

This invention provides a method of determining the fatigue status of the metallic specimen at just about any point during its service life. The method includes contacting the specimen with a cell containing an electrolyte and an electrode. A voltage is then generated between the specimen and the electrode, either by applying it externally or by relying upon the specimen and electrode to generate a current galvanically, and the electrical current is measured as it passes through the cell during a period of cyclic deformation. This measured current is thereafter used to prepare a signature which is representative of a fatigue status of the specimen.

The methods and devices of this invention can be used for analyzing the extent of fatigue damage in a metallic specimen. These procedures can be used to determine if the specimen is in the rapid hardening, saturation, crack nucleation, or crack propagation stages of its fatigue life. When compared to non-destructive testing techniques, the procedures of this invention provide a means for detecting fatigue damage long before a crack initiates. This invention also represents a significant improvement over fatigue strain gauges and fuses which, by their very nature, must be used with new metallic structures. Accordingly, the methods and devices of this invention can be used for determining the remaining fatigue life of various metal-containing structures, including aluminum airplane components, turbine shafts, and structural bridge components.

In further aspects of this invention, devices are provided for determining a fatigue status of a metal or alloy specimen. The devices include a module containing an electrode and an electrolyte disposed in contact with a surface of the specimen or structure. A voltage source is also provided for creating an electrical potential between the electrode and the specimen surface. This device could be adapted for detecting cracks or similar flaws in new structures, or for evaluating the substrate cracking behavior or integrity of conductive and nonconductive coatings, paints, or oxide layers.

BRIEF DESCRIPTION OF THE DRAWINGS

The accompanying drawings illustrate preferred embodiments of this invention so far devised for the practical application of the principles thereof, and in which:

FIGS. 6a–6c are experimental curves for a polycrystalline 316L stainless steel specimen, tested in the transition region, $\epsilon_{pl}=0.001$, for a current transient curve; strain curve; and stress curve respectively;

DETAILED DESCRIPTION OF THE INVENTION

Figure 1:
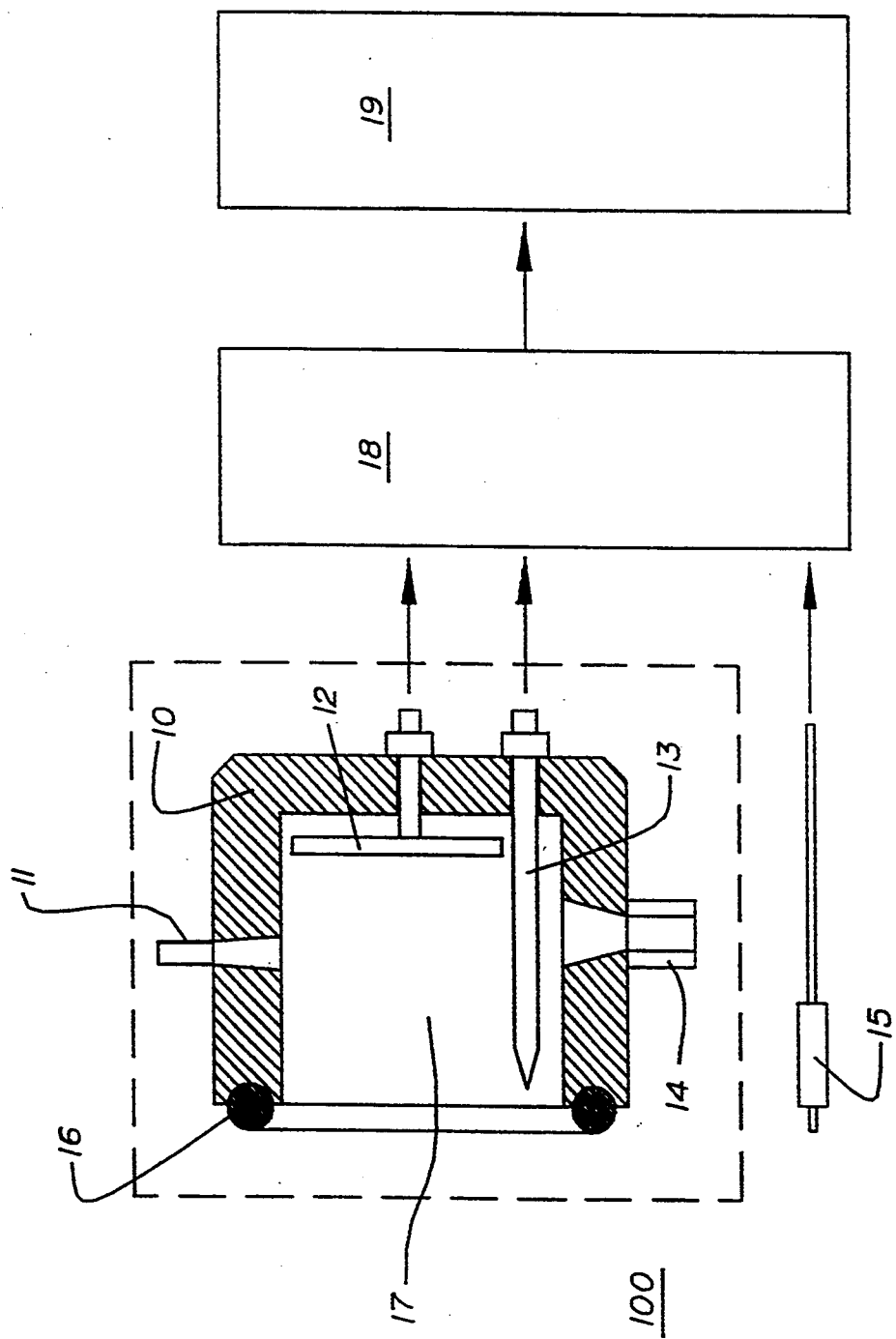
FIG. 1 is a cross-sectional, diagrammatic, side view of a preferred fatigue gauge of this invention.

With reference to FIG. 1, there is shown a preferred fatigue gauge 100 of this invention having a module 10 and a plurality of electrical contacts, including a counter electrode 12, a reference electrode 13, and a working electrode 15. The module 10 is equipped with a solution inlet 14 and an air outlet 11 for introducing an electrolytic solution, such as liquid electrolyte 17. In order to provide a seal against a specimen surface, an o-ring 16 is provided in an annular cavity along the mouth of the module 10.

During use, the gauge 100 operates by directing a current along the working electrode 15, which in turn, feeds through the specimen surface and into the electrolyte 17. When the specimen is stressed, such as when it undergoes elastic or plastic tensile and compressive stresses, the metal will undergo enhanced dissolution of atoms into the electrolyte. Upon plastic deformation of the specimen surface, additional areas are created from which dissolution of atoms occurs more readily than for the relatively unstrained surface. It is this phenomenon that is controlled and advantageously employed for determining the fatigue status of various metallic substrates in accordance with this invention.

Figure 5:
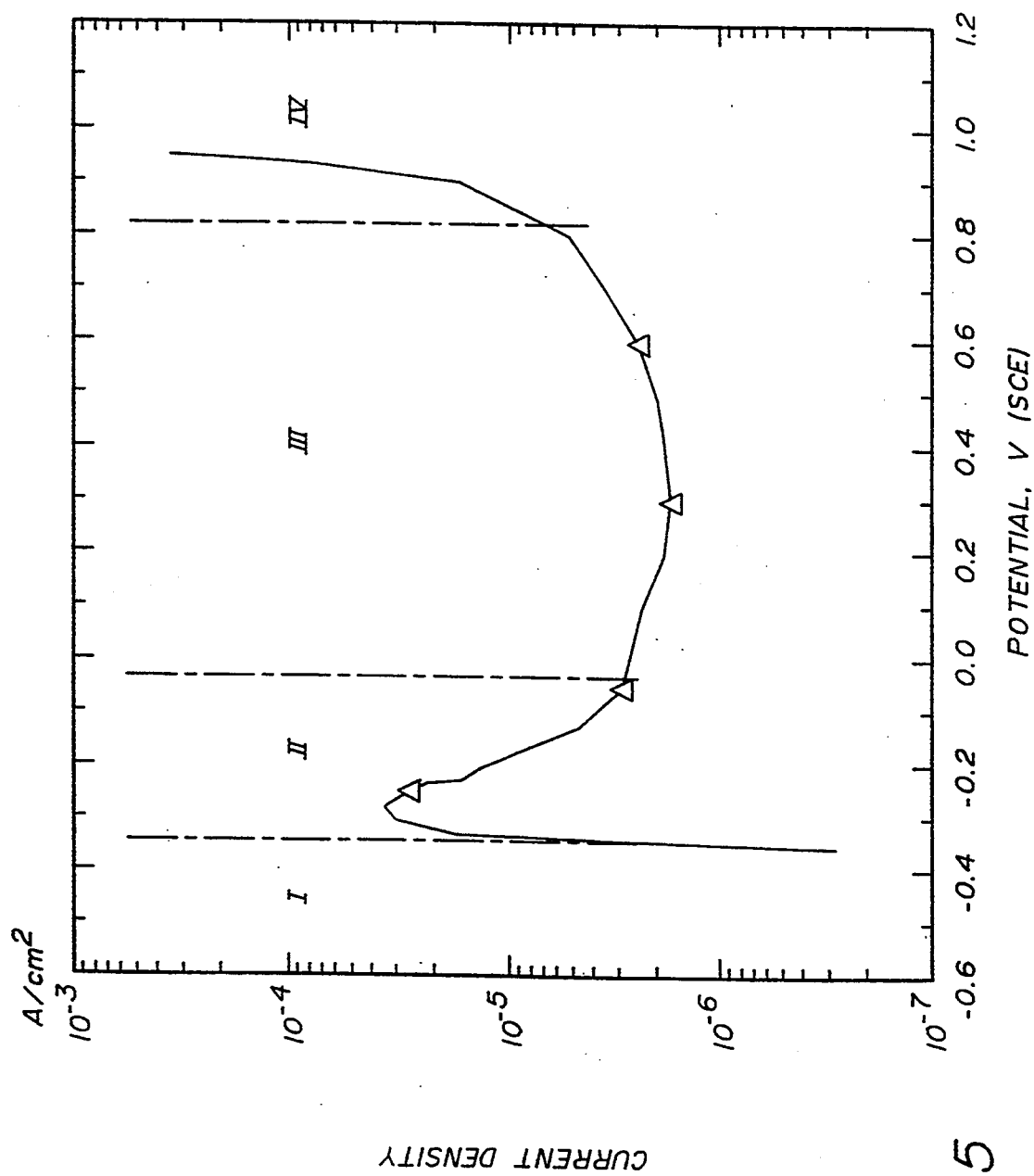
FIG. 5 is a graphical depiction of a polarization curve for an AISI 316L stainless steel specimen, wherein the $\Delta$ symbols represent select potentials chosen for the fatigue testing.

The fatigue gauge 100 preferably includes a three-electrode arrangement to maintain accurate potential control. A working electrode 15 is provided in contact with the specimen. This electrode is preferably connected with a control unit 18. The end of the working electrode 15 can include connection means, such as an alligator clip, for mechanically joining the electrode 15 to the surface of the specimen. The counter electrode 12, on the other hand, is located within the module 10 and preferably includes a large surface area having a disk-like appearance, the counter electrode 12 is preferably positioned near the rear of the module 10 and is electrically connected to the control unit 18. Finally, the reference electrode 13 can be used to provide a constant anodic potential preferably selected from the four distinct regions of the polarization curve: cathodic, active, passive, and transpassive regions respectively, as shown in FIG. 5.

The control unit 18 preferably includes means, such as a potentiostat, for determining variations in the corrosion current caused by applied strains during the fatigue life of the specimen. This current is referred to as the "transient current" of the system. The control unit operates with a current monitor 19 which preferably provides electricity, checks the continuity of the system, and provides data storage means for recording the measured transient currents. The stored currents can be plotted, using an X-Y recorder and a chart recorder, to provide a signature of the fatigue status of the specimen. Although the preferred "signature" is a curve generated from indicia of a measured transient current, it could also be any recorded data that can be subsequently converted or analyzed mechanically, electronically, or visually to provide a measure of fatigue status. For example, the current could be measured so that when the measured amplitudes reach a certain minimum amount, or a crack spike is detected, a visual or audible alarm would be activated.

Figure 3:
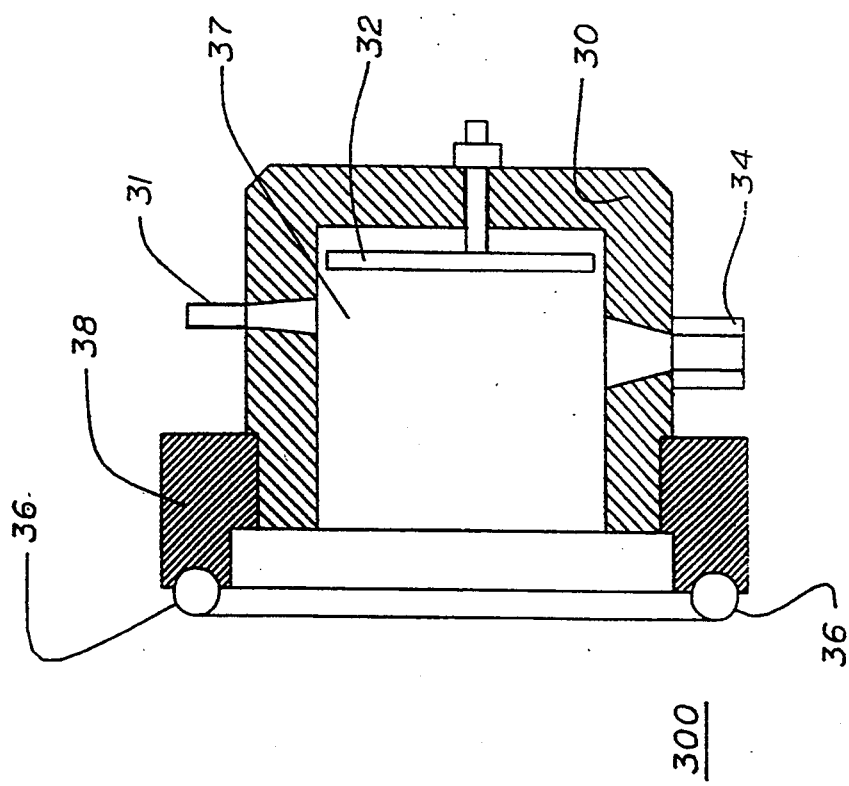
FIG. 3 is a cross-sectional, diagrammatic, side view of an additional fatigue gauge of this invention.
Figure 2:
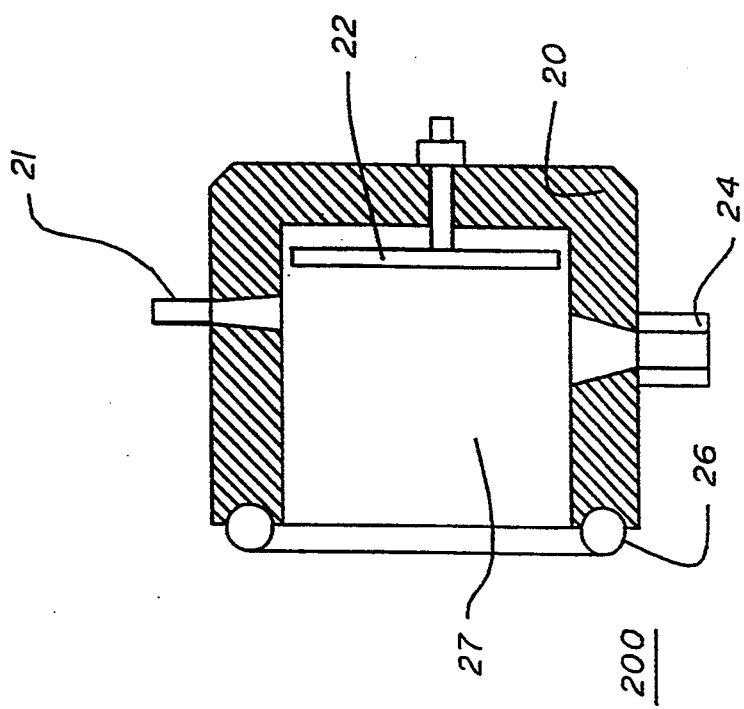
FIG. 2 is a cross-sectional, diagrammatic, side view of an alternative fatigue gauge of this invention.

With reference to FIGS. 2 and 3, there is shown alternative fatigue gauges 200 and 300 of this invention. Fatigue gauge 200 is a simpler, two-electrode variant which could be employed when preliminary tests have already identified the optimal measuring conditions, such as the optimum potential. This embodiment includes a module 20 having an air outlet 21 and a solution inlet 24. A counter electrode 22 is also provided, but since the optimum potential has already been identified, a reference electrode is not necessary. As with the fatigue gauge 100, this gauge 200 includes an electrolyte 27 and an o-ring seal 26.

In a further embodiment of this invention, a larger fatigue gauge 300 is provided. This gauge also includes an electrolyte 37 contained within a module 30 having a solution inlet 34 and an air outlet 31. An additional annular supporting lip 38 and an o-ring seal 36 are provided to assist in sealing the module 30 against a specimen. As can be readily observed, this gauge 300 accommodates a larger sensing area.

The specimens of this invention can be both experimental and commercial metal-containing substrates. Examples include test specimens made from raw stock, or specimens taken from existing structures during their useful service life. Alternatively, the commercial structures themselves can be the basis for the test specimen, for example, an exposed surface of an airplane skin or structural bridge member. The specimen should, nevertheless, have a conductive surface thereon. It can consist of a metal-containing polymer or composite, as well as an assortment of metals, such as, carbon steel, stainless steel, copper, aluminum, titanium, and their alloys. These polymers and metals can also contain a coating, such as a paint, resin, oxide, or passivation layer.

The modules 10, 20, and 30 of this invention preferably are "cup-shaped", and include a large opening at one end for Contacting the metallic specimen with the contained electrolyte 17, 27, and 37. The shape of the module is arbitrary, and can range from a variety of shaped rigid or flexible members adapted to seal against a flat or irregularly-shaped metallic article. It is further anticipated that the article itself may contain a cavity suitable for housing an electrolyte, in which case, the module may be nothing more than a flat plate sufficient to contain and seal the electrolyte in the metal cavity. The module is preferably made of a non-conductive ceramic or polymeric material, and preferably is corrosion-resistant. Preferred materials include polyethylene, polycarbonate, PTFE, polyimide, and polyamide, for example.

The electrolyte 17, 27, and 37 can be any electrolytic substance that is capable of conducting current, and preferably is capable of dissociating into ions in solution to become electrically conductive. Liquids, such as aqueous salt solutions and acids, and gels are preferred, with the latter being especially adapted for high temperature service. The preferred pH depends on the metal, but for corrosion-resistant metals, is less that about 4, with a pH below 2 being more conducive to ions releasing from the metal specimen preferred. However, depending on the sensitivity of the specimen to corrosion, pH values equal to or greater than 7 could be used, and even a natural aqueous corroding medium in applications, for example, where a structure is submerged, or contains a corroding medium.

EXAMPLE

The material used in this study was commercial, polycrystalline AISI 316L stainless steel.

Figure 4:
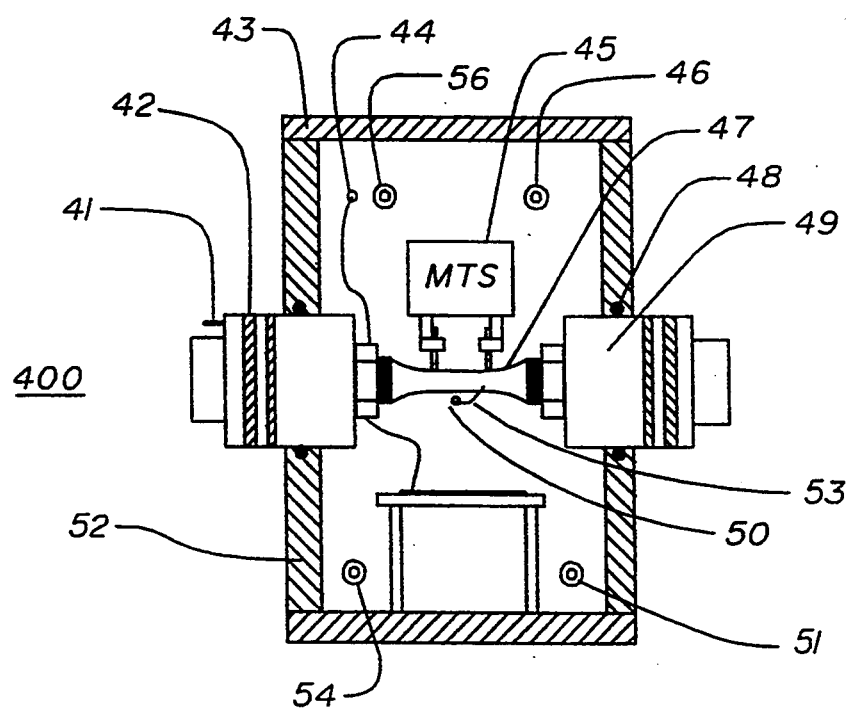
FIG. 4 is a cross-sectional, diagrammatic, side view of a testing apparatus used to demonstrate the principles of the instant invention.

The configuration of the test specimens was a 3.5 mm diameter, threaded test bar 47 as shown in FIG. 4. In some of the specimens, a planar region was spark cut on the gauge length, in order to produce a flat surface for good SEM observation. The specimens were annealed in vacuum at 1050° C. for one hour, then quenched in water. Then the surfaces of the specimens were polished mechanically and electrolytically.

The electrolytic environment chosen was 1N $H_2SO_4$ solution with a pH value of 0.4 (±0.01). The reason for choosing this solution is that distinct reactions can be identified easily by controlling the applied potentials. The low pH value employed ensured that an active region appeared in the polarization curve. In order to maintain rigorous control of the electrochemical conditions, dissolved oxygen was removed before each fatigue test by deaerating the solution. The electrolytic solution and purified argon gas were kept flowing through the environment chamber during the experiment. The argon inlets 46 and 54 and outlet 56, and the solution inlet 51 were used for this purpose.

Corrosion fatigue tests were performed by controlling the mechanical and electrochemical parameters, i.e., the plastic strain amplitude and the polarization potentials. Correspondingly, a special testing apparatus shown in FIG. 4 was designed to keep the specimen under well controlled corrosion fatigue conditions.

The testing apparatus 400 is one element of four main parts, which included a mechanical testing machine; solution deaeration and argon purification system;- potential control electronics; and data recording system.

Cyclic deformation of the specimens was carried out by an MTS servo-controlled electrohydraulic fatigue machine. In order to protect the extensometer 45 from damage by the corrosive solution, as explained below, a horizontal arrangement was adopted.

A carefully designed environmental chamber was used both to immerse the specimen 47 in the aqueous environment and to maintain the specimen and solution in an argon atmosphere. The body of the chamber consisted of two side walls 52 made of polytetrafluoroethylene ("PTFE"), and one cylindrical shell 43 made of PLEXIGLASS® which allowed direct observation of the specimen-electrode assembly during a test.

On the wall of the chamber's shell, inlets and outlets were provided for leading both the deaerated solution and purified argon gas through the chamber. A dam was constructed near the solution outlet to maintain the solution at such a level that the entire sample was immersed in the solution, whereas the body of the extensometer 45 was kept outside the corrosive solution. The two knives of the extensometer, which were attached directly to the gauge section of the specimen were made of ceramic to prevent interference with both the potentiostat control system and the MTS control system. An argon inlet, provided at the bottom of the chamber was used to bubble argon gas through the solution during cathodic treatment before a fatigue test, in order to minimize the effect of the hydrogen gas produced as a by-product during cathodic treatment.

The specimen 47 was mounted by locking nuts into two grips 49 made of AISI 304 stainless steel and sealed with o-rings 48. Two pieces of PTFE insulation 42 were inserted between the metal parts of the grips 49 to ensure that the testing cell was electrically isolated from the testing machine. The heads of the grips and locking nuts were covered by PTFE shells and caps in order to keep the specimen 47 electrochemically separated from any of the other metals of the testing equipment. The whole set of grips 49 and specimen 47 was mounted in the MTS machine by locking nuts using a Wood's alloy pot for stress free insertion of the specimen.

Deaeration was accomplished by bubbling purified argon gas through the solution in the solution supply tank for several hours before, a fatigue test, and this treatment was continued during the test.

Purified argon was obtained by passing stock gas through drierite and then through furnace-heated copper turnings at about 450° C. The purified argon was then supplied to the solution tank and the testing cell for solution deaeration and chamber flushing respectively.

A PAR (Princeton Applied Research), model 173 standard potentiostat was used to obtain precise potential measurement and control. It was also equipped with a PAR model 175 Universal Programmer for carrying out the potential polarization (sweeping) test.

The three-electrode method was employed for the tests to maintain accurate potential control. The working electrode was the specimen 47 itself, which was connected to the potentiostat (not shown) through the grip 49 and exited through outlet 41. The counter electrode 44 was a platinum gauze positioned near the bottom of the chamber. The reference electrode 53 was inserted through inlet 50 and consisted of a saturated calomel electrode coupled with a salt-bridge.

The hysteresis loop of the deformation was monitored by a Tektronix model 5223 digital oscilloscope. These loops were also recorded by an X-Y recorder for hardening and saturation analysis. The current transient wave form and the strain cycling wave form were recorded simultaneously by a Gould Brush 2400 two channel strip chart recorder.

After polishing, the specimen 47 was cleaned in methanol, and dried. The surface of the specimen was then wrapped with PTFE tape at its ends, leaving a known area uncovered in the gauge length for the measurement of current density.

After being mounted in the MTS machine, the specimen was cathodically treated at about −0.7 V (SCE) for 30 minutes to clean the exposed surface. During this period, purified argon was introduced into the chamber through the argon inlet 54 at the bottom of the chamber, to blow out the hydrogen bubbles from the specimen surface. The potential was then switched to that desired-for testing, and held steady for about 30 minutes to reach a stabilized current for beginning the test.

The fatigue test was conducted under plastic strain amplitude control, with a sinusoidal wave form. The frequency of cycling was chosen to be about 0.5 Hz. In most cases, the plastic strain amplitude was set at about 0.001, which was determined according to the cyclic stress-strain curve (CSSC) obtained in air. In order to determine the contribution from elastic deformation to the transient current, some fatigue tests were performed at a total strain amplitude below the elastic limit.

The electrochemical conditions of the tests were controlled at constant anodic potentials, which were chosen from the polarization curve obtained by a potential sweep test. The polarization curve of AISI 316L stainless steel, FIG. 5, consists of four distinct regions: cathodic, active, passive, and transpassive regions respectively. The active and passive regions proved to be the most interesting. In order to improve our understanding of electrochemical/ mechanical interactions, four potentials were chosen for performing corrosion fatigue tests, as indicated by the small triangles in FIG. 5. −0.25 V was chosen as the corrosion potential, −0.05 V as the active/passive transition potential, +0.3

V as the passive I potential and +0.6 V as the passive II potential, respectively. All of these potentials were measured at the saturated calomel electrode (SCE).

One of the most important consequences of corrosion fatigue is that the corrosion rate of the material was shown to be greatly enhanced by the cyclic deformation. Accordingly, a variation in the corrosion current with applied strain was determined. Although the surface reaction will change with different applied potentials, some features of the current transient behavior, observed by analyzing the current data recorded at different potentials, were found to be common to the different potentials.

During corrosion fatigue tests, the transient current was observed to vary with mechanical cycling for all stainless steel polycrystalline specimens. Very small current levels were recorded. Such variations were observed at all four potentials shown in FIG. 5. A typical example of current behavior is shown in FIGS. 6a–6c. One polycrystalline specimen was cycled at a potential of −0.05 V (SCE) with a plastic strain amplitude of $\epsilon_{pl}=1\times10^{-3}$. The specimen was deformed in the tensile direction first. During the first cycle, the current showed a small transient (arrowed) towards the negative direction at the very start of deformation, but it then increased very quickly to a maximum value followed by a rapid reduction or decay. The frequency of the current cycling was found to be two times that of the mechanical cycling.

As indicated by FIG. 6a, there are two current peaks in each fatigue cycle, which lie at positions a little earlier than the maximum values of the strains for both tension and compression. The capital letters "T" and "C" are used to identify the maximum values in the current versus time curves as a tension peak and a compression peak respectively. As the cycling proceeded, the height of the current peaks decreased gradually with the increased number of cycles. A relatively stable value of the current peak was reached after thousands of cycles. Apparently, these current peaks were produced by plastic deformation both in tension and compression.

As shown in FIG. 6a, the tension peak was higher than the compression peak, especially for the beginning several cycles. This is believed to be caused by the well-known tension-compression asymmetry in stress, which favors plastic deformation in the tensile direction.

Figure 8A:
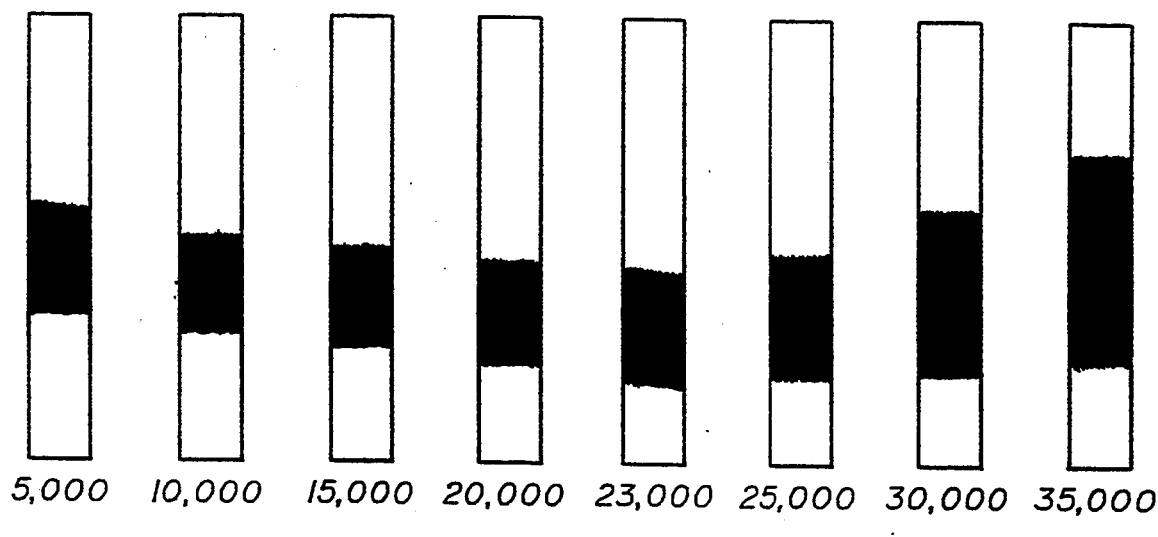
FIGS. 8a–8c are graphical depictions of a polycrystalline 316L stainless steel specimen fatigue tested in the passive I region, $\epsilon_{pl}=0.001$, for the current transient curve; current wave form at 30,000 cycles; and current wave form at 35,000 cycles respectively.
Figure 8B:
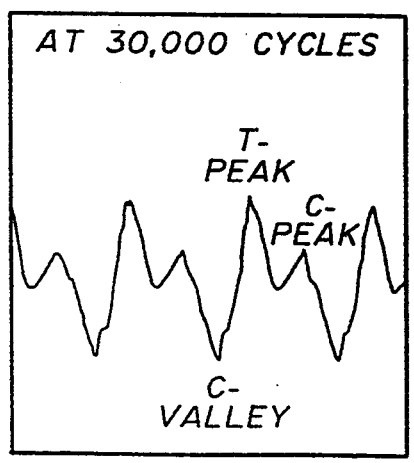
Figure 8C:
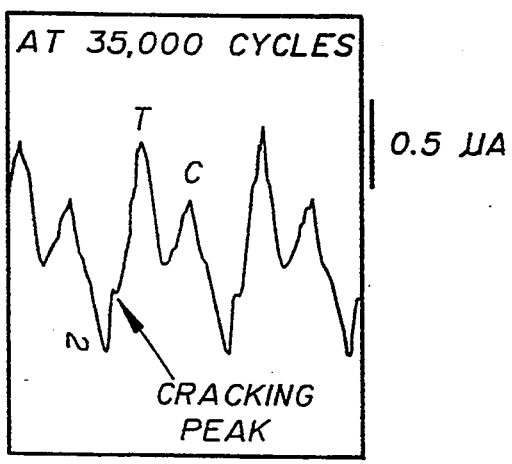

Another important feature of the current transient curve is the different value of the minimum following each current peak shown in FIG. 6a. For convenience, the minimum after the tension peak is referred to as the T-valley, and the other minimum is referred to as the C-valley. It was found that the value of the T-valley was always higher than that of the C-valley, no matter which potentials were used, and no matter where in the number of cycles they were observed during the test. The difference between the values of the two valleys changed little during the test, except when the fatal cracks had developed and grew very quickly as shown in FIGS. 8b and 8c.

The modification of the current transient curve by the two current valleys is indicative of the fatigue status of the specimen, since it has an almost direct correlation with the number of cycles to which the specimen has been subjected to. For example, in FIG. 6, the three columns of tracings record behavior at different numbers of cycles, the left column is at the start of cycling, and the 15th and 45th tensile strokes are labelled in the second and third columns to identify the cycle counts.

Figure 7:
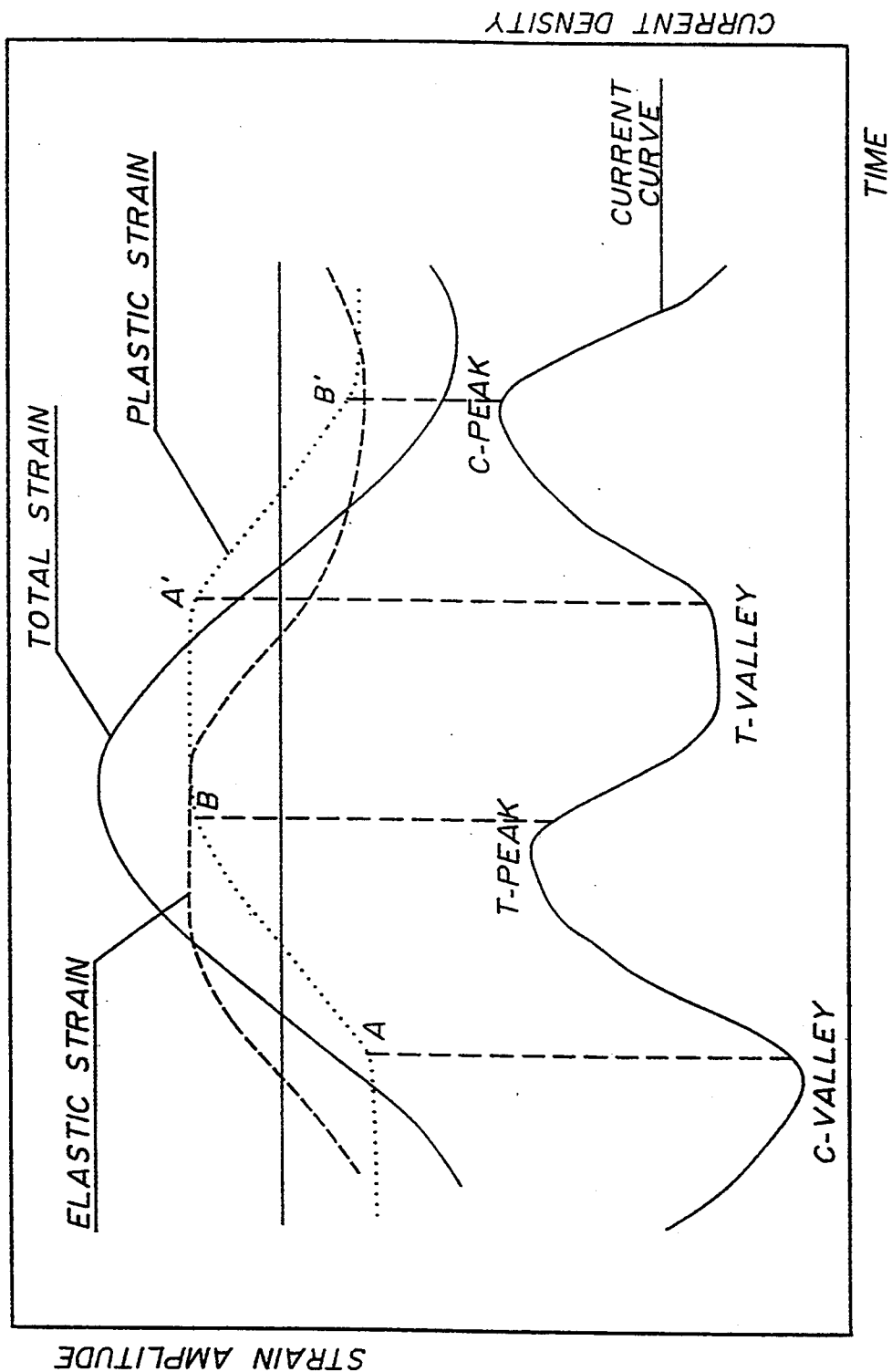
FIG. 7 is a graphical depiction of strain amplitude versus time for demonstrating the correspondence between strain and transient current.

Analysis was conducted with the current data obtained from a polycrystalline specimen, which was fatigued in the passive I region at about 1,000 cycles. In relating the current behavior to the components of the deformation, it is necessary to examine separately the effects of plastic strain and elastic strain. As shown in FIG. 7, the current transient can be divided into two components: current associated with plastic strain (CAPS) and current-associated with elastic strain (CAES). The CAPS has two peaks during one mechanical cycle, which correspond to the plastic deformation in tension and in compression respectively. The CAES has only one peak in each cycle which usually lies at the position between the maximum compression strain rate and the maximum compression strain. The values of these strains are plotted against time in FIG. 7. Also included in this figure is the current transient curve.

From this curve, it can be seen that the major part of the current variation was caused by the plastic straining. At point A, which represents the yield point in the cycling, the plastic strain is maximum in compression. From point A to point B, the specimen undergoes plastic deformation from maximum compression to maximum tension. During this period, fresh metallic surface continuously emerged on the gauge section and, in association, the anodic current increased rapidly, i.e., the T-peak occurred in the current transient curve. From point B to point A', the plastic straining was temporarily halted, the specimen elastically relaxed from maximum tension to zero, and then underwent strain in compression. Correspondingly, the anodic current decayed rapidly to a minimum value (the T-valley in the current transient curve) From point A' to B', the specimen was plastically deformed in compression, and fresh surface again emerged as in the tensile period. Therefore, a C-peak showed up, followed by a C-valley when the cyclic process continued from point B' to A. The difference between the values of the T-valley and C-valley is due to the elastic stress or strain. The positions of the T-valley and C-valley lie at positions corresponding to the maximum strain rate on the elastic strain curve.

It is possible in some structures where the electrochemical properties of the metal are of such a kind, or the fatigue damage so limited in area fraction, that the CAES could overwhelm the fatigue signature component of the measured current in a large background. In such a case, a non-conductive coating could be applied to the specimen to suppress this background, and intrusion of the fatigue damage through the coating could be sensed. The same approach could be used to protect a corrosive sensitive specimen from potentially damaging effects of the fatigue sensing device.

The following conclusions can be drawn here about the general features of the transient current. During cycling, the major part of the current variation comes from the plastic deformation, and is closely related to the exposure of the fresh metal surface to the corrosive solution. The reactivity of the newly exposed area with the solution is much higher than that of the pre-existing surface. The conclusion is that the differences in compositions and atomic arrangements between the newly formed area and the gross external surface of the specimen are responsible for the big difference in their reactivities.

Another important feature of the current transient curve is that crack nucleation and growth can be monitored by close inspection of the shape of the current curve. An example of this shape effect is given in FIGS. 8a–8c, in which a current-cycle recording is shown for polycrystalline specimen cycled in the passive I region. After 25,000 cycles in this specimen, cracks nucleated and began to grow. Accordingly, the current amplitude, $j_T$ or $j_C$, began to increase (FIG. 8a). (Notice that the curve in FIG. 8a was recorded at a very low chart speed, therefore the current recording pen sweeps an area defined by the T-peak and C-valley.) At about 30,000 cycles, a fatal crack could be identified by the presence of a small "bump" located at the bottom of the C-valley (FIG. 8b). As the cycling proceeded, the bump gradually enlarged until final failure occurred (FIG. 8c).

Figure 9:
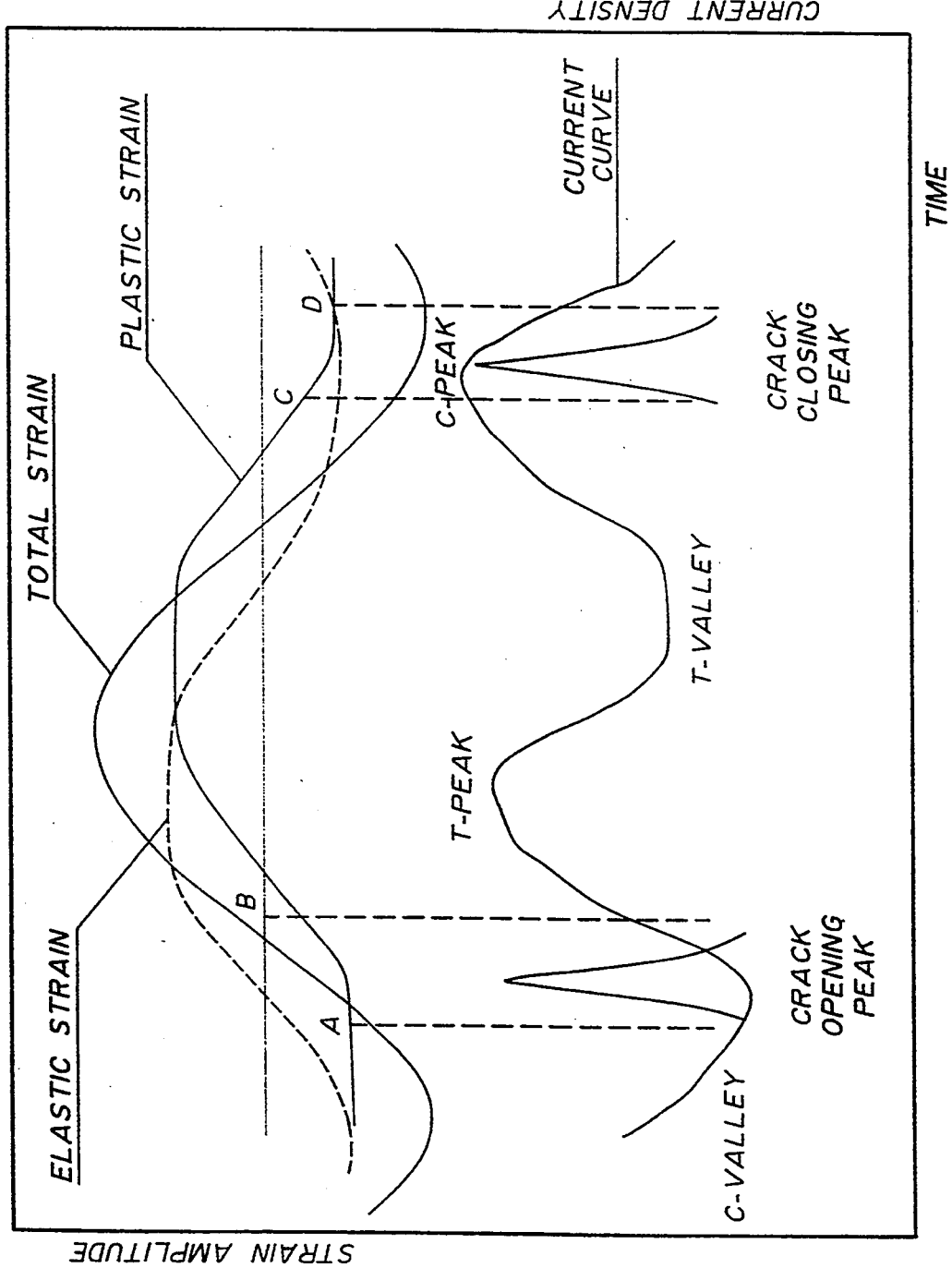
FIG. 9 is a graphical depiction illustrating the phase relationship between the current peaks and strains.

An explanation for this crack-related current transient is as follows. During the tensile period, from point A to B in FIG. 9, the specimen deforms elastically, and the crack opens by plastic flow at the tip thus exposing a fresh area to the solution, which in turn produces an instant increase in current, followed by a rapid current decay. As the specimen continues to be plastically deformed in tension, the T-peak develops in the current curve. The crack-opening peak and the T-peak are separated by a period of time. Therefore, they can be distinguished. As the specimen cycles into compression, the crack closes first, followed by plastic deformation. Since cracks tend to close as the specimen is unloaded from tension, one would expect a bump to precede the C-peak, like in tension. However, this behavior is not observed. Rather, from point C to D, a current transient is produced due to a change in surface status around the cracking area, such as film rupture. However, this crack-closure transient coincides with the C-peak. Therefore, no current variation is seen in the T-valley; and the height of the C-peak increases. The shape of the crack induced peak in the current is noticeable and can be much sharper than that of the straining current peaks under optimum conditions, showing that the crack-induced peak is an instantaneous reaction. Broadened distributions of current observed in the straining peaks, especially the T-peak, are associated with the sequential emergence of many slip steps.

The above example demonstrating the correspondence between transient current and cyclic deformation in corrosion fatigue of an AISI 316L stainless steel leads to a number of conclusions. There is a strong interaction between the aqueous environment and the cyclic deformation, which can be perceived from transient current curves obtained during corrosion fatigue tests. The transient current can be divided into two components, the CAPS and the CAES respectively. The CAPS has two peaks in one mechanical cycle, corresponding to plastic deformation both in tension and in compression. The CAES varies periodically at a frequency the same as that of mechanical cycling. At a strain amplitude of $1 \times 10^{-3}$, the CAPS causes the major part of the current transient, which is produced by metallic dissolution at slip steps where the atomic composition is quite different from that on the average surface. The decrease of the current peak during the softening stage is caused by a gradually reducing tendency in the selective dissolution of iron. The different values of the T-peak and the C-peak in the current curve are produced partly by the tension-compression asymmetry and partly by cyclic creep, which favors plastic deformation in the tensile direction. The beginning of corrosion fatigue failure by cracking can be monitored by close inspection of the transient current curve. Elastic strain or stress can cause current variation by changing the energetic status of the atoms on the specimen surface, which is important to corrosion fatigue at low strain amplitude. There is a possibility that a charging effect of the electric double layer has a noticeable contribution to the CAES.

From the foregoing, it can be realized that this invention provides fatigue gauges and methods for determining the fatigue status of metallic elements at any point during their useful life. The electrochemical techniques used by this invention are highly sensitive and can even isolate the onset of fatigue cracking in specimens long before catastrophic failure. Although various embodiments have been illustrated, this was for the purpose of describing, and not limiting the invention. Various modifications, which will become apparent to one skilled in the art, are within the scope of this invention described in the attached claims.

What is claimed is:

1. A method of determining the fatigue status of a metallic specimen, comprising:
   contacting said specimen with a cell containing an electrode and an electrolyte in contact with said specimen;
   applying a voltage between said specimen and said electrode;
   subjecting said specimen to a deformation cycle;
   measuring a current passing through said electrolyte during said cycle;
   preparing a signature representative of said measured current, said signature comprising elastic and plastic deformation transient current components; and
   analyzing said signature to determine the fatigue status of said specimen, said analyzing step comprising determining the presence of a crack in said specimen by isolating a current spike in said current curves.

2. The method of claim 1, wherein said analyzing step comprises comparing said signature to a known measured current signature for a substantially similar metallic substance.

3. The method of claim 1, wherein said metallic specimen comprises a structural steel member subject to atmospheric conditions.

4. The method of claim 3, wherein said cyclic deformation cycle comprises tensile and compressive plastic strain.

5. A method of determining the fatigue status of a metallic specimen, comprising:
   contacting said specimen with a cell containing an electrode and an electrolyte in contact with said specimen;
   applying a voltage between said specimen and said electrode;
   subjecting said specimen to a deformation cycle;
   measuring a current passing through said electrolyte during said cycle;
   preparing a signature representative of said measured current, said signature comprising elastic and plastic deformation transient current components; and
   analyzing said signature to determine the fatigue status of said specimen, wherein said analyzing step determines whether said specimen is in the rapid hardening, saturation, crack nucleation, or propagation stages of fatigue deformation.

6. The method of claim 5, wherein said signature comprises a plurality of tensile and compressive current peaks decreasing in amplitude with the number of cycles of said deformation cycle.

7. A method of electrochemically determining the corrosive fatigue status of a metal or alloy specimen subject to cyclic deformation, comprising:
   contacting said specimen with a module containing an electrolyte and an electrode;
   connecting said specimen to a source of reference potential;
   passing an electrical current through said electrolyte between said specimen and said electrode;
   measuring said current over a plurality of deformation cycles including tensile and compressive forces;
   preparing a plurality of transient current curves indicative of a fatigue response of said specimen; and
   determining said fatigue status of said specimen by analyzing the presence of a crack in said specimen by isolating a current spike during said deformation cycles.

8. The method of claim 7, wherein said electrical current is selected to dispose said specimen within an active or passive region of its polarization curve.

9. The method of claim 7, wherein said electric potential is less than about 10 volts.

10. The method of claim 7, wherein said electric potential is less than about 1 volt.

11. The method of claim 7, wherein said determining step compares said transient current curves with known fatigue data previously generated for a substantially similar specimen.

12. The method of claim 7, wherein said cyclic deformation comprises plastic tensile and compressive forces.

13. The method of claim 7, wherein said corrosive environment comprises a liquid or gelatinous electrolyte.

14. The method of claim 13, further comprising monitoring said current over a significant portion of the fatigue life of said specimen.

15. The method of claim 7, wherein said specimen comprises a coating, paint, passivation, or oxidation layer.

16. A method of determining the fatigue status of a metallic specimen, comprising:
   contacting said specimen with a cell containing an electrode and an electrolyte in contact with said specimen, said specimen and said electrode producing a galvanic reaction;
   subjecting said specimen to a deformation cycle;
   measuring a galvanic current passing through said electrolyte during said cycle;
   preparing a signature representative of said measured current, said signature comprising a plurality of current curves comprising elastic and plastic deformation transient current components; and
   analyzing said signature to determine whether said specimen is in the rapid hardening, saturation, crack nucleation, or propagation stages of fatigue deformation.

17. The method of claim 16, wherein said analyzing step comprises comparing said signature to a known measured current signature for a substantially similar metallic substance.

18. The method of claim 17, wherein said metallic specimen comprises an anode and said electrode comprises a cathode of said galvanic reaction.

* * * * *